United States Patent [19]

Nicolau et al.

[11] Patent Number: 6,107,514
[45] Date of Patent: Aug. 22, 2000

[54] VINYL ACETATE PRODUCTION USING A CATALYST COMPRISING PALLADIUM AND GOLD DEPOSITED ON A COPPER CONTAINING CARRIER

[75] Inventors: Ioan Nicolau; Adolfo Aguilo; Philip M. Colling, all of Corpus Christi, Tex.

[73] Assignee: Celanese International Corporation, Dallas, Tex.

[21] Appl. No.: 09/340,822

[22] Filed: Jun. 28, 1999

Related U.S. Application Data

[62] Division of application No. 08/867,911, Jun. 3, 1997.

[51] Int. Cl.[7] ............................ C07C 67/05; C07C 67/02
[52] U.S. Cl. ............................................. 560/245; 560/261
[58] Field of Search .................................... 560/245, 261

[56] References Cited

U.S. PATENT DOCUMENTS

| | | | |
|---|---|---|---|
| 4,087,622 | 5/1978 | Nakamura et al. | 502/170 |
| 4,119,567 | 10/1978 | Bartsch | 502/331 |
| 4,764,498 | 8/1988 | Wissner et al. | 502/251 |
| 5,185,308 | 2/1993 | Bartley et al. | 502/170 |
| 5,274,181 | 12/1993 | Bartley et al. | 560/245 |
| 5,332,710 | 7/1994 | Nicolau et al. | 502/243 |
| 5,347,046 | 9/1994 | White et al. | 560/245 |
| 5,422,329 | 6/1995 | Wirtz et al. | 502/328 |
| 5,731,457 | 3/1998 | Nicolau et al. | 560/245 |

FOREIGN PATENT DOCUMENTS 1246015  9/1971  United Kingdom .

*Primary Examiner*—Gary Geist
*Assistant Examiner*—Robert W. Deemie
*Attorney, Agent, or Firm*—M. Susan Spiering

[57] ABSTRACT

Synthesying vinyl acetate utilizing a catalyst for the production of vinyl acetate by reaction of ethylene, oxygen and acetic acid comprising a porous support on the porous surfaces of which is deposited metallic copper in a zone surrounded by deposits of catalytically effective amounts of metallic palladium and gold, neither of which is substantially intermingled with said copper.

11 Claims, No Drawings

VINYL ACETATE PRODUCTION USING A CATALYST COMPRISING PALLADIUM AND GOLD DEPOSITED ON A COPPER CONTAINING CARRIER

The present invention is a divisional of U.S. Ser. Application No. 08/867,911 filed Jun. 3, 1997.

BACKGROUND OF THE INVENTION

1. Field of the Invention

This invention relates to a new and improved catalyst for the production of vinyl acetate by reaction of ethylene, oxygen and acetic acid.

2. Background Information Including Description of Related Art

It is known to produce vinyl acetate by reaction of ethylene, oxygen and acetic acid using a catalyst consisting of palladium, gold and copper supported on a carrier. While the process utilizing such a catalyst is capable of producing vinyl acetate at relatively high levels of productivity, any expedient resulting in even greater productivity over the life of the catalyst would be very desirable.

The following references may be considered material to the invention claimed herein.

U.S. Pat. No. 5,332,710, issued Jul. 26, 1994 to Nicolau et al., discloses a method of preparing a catalyst useful for the production of vinyl acetate by reaction of ethylene, oxygen and acetic acid, comprising impregnating a porous support with water soluble salts of palladium and gold, fixing the palladium and gold as insoluble compounds on the support by immersing and tumbling the impregnated support in a reactive solution to precipitate such compounds, and subsequently reducing the compounds to free metallic form.

U.S. Pat. No. 5,347,046, issued Sep. 13, 1994 to White et al., discloses catalysts for the production of vinyl acetate by reaction of ethylene, oxygen, and acetic acid, comprising a palladium group metal and/or a compound thereof, gold and/or a compound thereof, and copper, nickel, cobalt, iron, manganese, lead or silver, or a compound thereof, preferably deposited on a support material.

SUMMARY OF THE INVENTION

In accordance with this invention, a catalyst is provided useful for the production of vinyl acetate by reaction of ethylene, oxygen and acetic acid with low carbon dioxide selectivity, comprising a porous support on the porous surfaces of which is deposited metallic copper in a zone surrounded by catalytically effective amounts of metallic palladium and gold, neither of which is substantially intermingled with the copper. The catalyst of the invention loses less of its copper by volatilization during long term use, resulting in less of a rise in carbon dioxide selectivity, and therefore less of a loss of vinyl acetate productivity due to such use, than when an equivalent supported palladium-gold-copper catalyst is used, except that the copper present on the support is substantially intermingled with one or both of the palladium and gold, due to the coprecipitation (fixing) of the copper on the support with one or both noble metals.

DETAILED DESCRIPTION OF THE INVENTION

Related to the invention claimed herein is the discovery, not appreciated heretofore, that during the production of vinyl acetate using a supported palladium-gold-copper catalyst wherein the copper is substantially intermingled with one or both of the palladium and gold, the copper content of the catalyst tends to be substantially reduced during the life of the catalyst, i.e., before it is necessary to replace or regenerate the catalyst, which may approach or exceed two years. Such loss of copper is apparently due to the fact that under reaction conditions, the copper which is at or near the surface of the catalyst particles, reacts with one or more of the reactants to form a compound with a tendency to sublime. In the catalyst of the invention, however, the copper is fixed on the support surfaces before the palladium and gold which largely surround the copper and cause it to be less exposed to ambient conditions within the reactor. Any sublimed copper compound which forms therefore has less opportunity to disperse into the reactor and the vapor pressure of such copper compound is therefore close to the partial pressure of the sublimed copper compound in the immediate surroundings. This causes less copper to be lost from the copper by sublimation than when the copper is intermingled with one or both noble metals at or near the surface of the catalyst particles. In this connection, it is noted that while the carbon dioxide selectivity of a vinyl acetate process utilizing any supported palladium-gold catalyst tends to rise during the life of the catalyst, i.e., from the time fresh catalyst is charged to the reactor to the time the reactor is shut down for the purpose of replacing or regenerating the catalyst, such carbon dioxide selectivity is generally lower during any point in the life of the catalyst when the catalyst contains a certain amount of copper in addition to palladium and gold than when no copper or less copper is present. Thus, the loss of a smaller amount of copper during the life of a catalyst under this invention results in higher overall vinyl acetate productivity than when employing a platinum-gold-copper catalyst in which the copper is intermingled with one or both of the noble metals at or near the surface of the catalyst particles.

In the preparation of the catalyst of this invention, a suitable porous catalyst support is first impregnated with an aqueous solution of a water-soluble copper salt, e.g., cupric nitrate trihydrate, cupric chloride, anhydrous or dihydrate, cupric acetate, cupric sulfate, or cupric bromide and the like. Impregnation techniques known in the art may be employed to impregnate the copper salt. Preferably, the impregnation can be accomplished by the "incipient wetness" method wherein an amount of copper compound solution used for the impregnation is from about 95 to about 100 percent of the absorptive capacity of the support material. The concentration of the solution is such that the amount of elemental copper in the impregnated solution is equal to a predetermined amount within the range, for example, of about 0.3 to about 5.0, preferably about 0.5 to about 3.0 grams/liter of catalyst.

The catalyst support material is composed of particles having any of various regular or irregular shapes, such as spheres, tablets, cylinders, rings, stars, or other shapes, and may have dimensions such as diameter length or width of about 1 to about 10 mm., preferably about 3 to 9 mm. Spheres having a diameter of about 4 to about 8 mm. are preferred. The support material may be composed of any suitable porous substance, e.g., silica, alumina, silica-alumina, titania, zirconia, silicates, aluminosilicates, titanates, spinel, silicon carbide, or carbon and the like.

The support material may have a surface area within the range, for example, of about 10 to about 350 m$^2$/g, preferably about 100 to about 200 m$^2$/g, an average pore size in the range, for example, of about 50 to about 2000 angstroms, and a pore volume in the range, for example, of about 0.1 to 2 ml/g, preferably about 0.4 to about 1.2 ml/g.

Following impregnation of the support with an aqueous solution of copper compound the copper is "fixed," i.e., precipitated, as a water-insoluble compound such as the hydroxide, by reaction with an appropriate alkaline compound, e.g., an alkali metal hydroxide, silicate, borate, carbonate or bicarbonate, in aqueous solution. Sodium and potassium hydroxides are preferred alkaline fixing compounds. The alkali metal in the alkaline compound should be in an amount, for example, about 1 to about 2, preferably about 1.1 to about 1.6 moles per mole of anion present in the soluble copper salt. The fixing of the copper may be done by techniques known in the art. Preferably, however, fixing of the copper is accomplished by the incipient wetness method wherein the impregnated support is dried, e.g., at a temperature of 150° C. for one hour, contacted with an amount of solution of the alkaline material equal to about 95–100% of the pore volume of the support, and allowed to stand for a period of about ½ hour to about 16 hours; or the roto-immersion method wherein the impregnated support without drying is immersed in a solution of the alkaline material and is rotated and/or tumbled during at least the initial period of precipitation such that a thin band of the precipitated copper compound is formed at or near the surface of the support particles. The rotation and tumbling may be carried out, for example, at about 1 to about 10 rpm for a period of about 0.5 to about 4 hours. The contemplated roto-immersion method is disclosed in U.S. Pat. No. 5,332,710, the intire disclosure of which is incorporated by reference.

Optionally, the support containing the fixed copper compound may be washed until there is essentially no trace of anions, e.g., halides in the catalyst, dried, e.g., in a fluidized bed drier at 100° C. or one hour, calcined, e.g., by heating in air at 200° C. or 18 hours, and reduced, for example, in the vapor phase by contacting the copper-containing support with a gaseous hydrocarbon such as ethylene (5% in nitrogen), e.g., at 150° for hours, or in the liquid phase by contacting the support before washing and drying with an aqueous solution of hydrazine hydrate containing an excess molar ratio of hydrazine to copper of, for example, about 8:1 to 12:1, at room temperature, for about 0.5 to about 3 hours, after which the support is washed and dried as described. Although any of the foregoing optional steps may be carried out singly or in combination to accomplish any desired purpose, such steps are often not necessary since the washing, drying and reduction of the copper compound can usually be adequately accomplished by the similar steps carried out on the palladium and gold compounds with which the copper containing support material is subsequently impregnated, as more finally described hereinafter.

The support material containing a zone of fixed insoluble copper compound, e.g., cupric hydroxide, or free copper metal with possibly some oxide, is then treated to deposit catalytic amounts of palladium and gold on the surfaces of the copper containing support particles. Any of various methods for accomplishing this purpose may be used, all of which involve simultaneous or separate impregnations of the support with one or more aqueous solutions of water-soluble compounds of palladium and/or gold. Palladium (II) chloride, sodium palladium (II) chloride, potassium palladium (II) chloride, palladium (II)nitrate or palladium (II) sulfate are examples of suitable water-soluble palladium compounds, while alkali metal, e.g., sodium or potassium salts of auric (III) chloride or tetrachloroauric (III) acid can be used as the water-soluble gold compounds. An alkali metal salt of tetrachloroauric (III) acid and sodium palladium (II) chloride are preferred because of their good water solubility. The quantity of these compounds employed is such as to provide, for example, about 1 to about 10 grams of palladium, and, for example, about 0.5 to about 10 grams of gold per liter of finished catalyst, with the amount of gold being from about 10 to about 125 wt. % based on the weight of palladium. The palladium and gold are then fixed to the copper-containing support material by treatment with an aqueous solution of an appropriate alkaline compound to precipitate the palladium and gold as water-soluble compounds such as the hydroxides, as described previously in connection with the prior fixing of copper on the support. Again, sodium or potassium hydroxide is preferred as the alkaline fixing compound, and the fixing or precipitation of water-insoluble palladium and gold compounds on the surface of the copper or copper compound containing support material may be accomplished by the incipient wetness method or the roto-immersion method as described previously in connection with the fixing of an insoluble copper compound on the support. The precipitated palladium, gold and copper (if not previously reduced) compounds may then be reduced, for example, with ethylene, e.g., 5% in nitrogen at 150° C. or 5 hours after first washing the catalyst containing the fixed metal compounds, until it is free of anions such as halide, and drying, e.g., at 150° C. or about 1 hour, or such reduction may be accomplished before washing and drying with an aqueous solution of hydrazine hydrate wherein the excess of hydrazine over that required to reduce all the metal compounds present on the support is in the range, for example, of about 8:1 to about 15:1, followed by washing and drying. Other reducing agents and means for reducing the fixed metal compounds present on the support may be employed as conventional in the art. The reduction of the fixed metal compound mainly results in the formation of the free metal, although a minor amount of metal oxide may also be present.

Alternative to the foregoing procedure, a "separate fix" method may be used to fix the palladium and gold on the copper-containing support and reduce the water-insoluble metal compounds to the desirable free metallic form. In this method, using the specific procedures described previously, the copper containing support is first impregnated with an aqueous solution of water-soluble compounds of palladium and any other catalytically active metal except gold which is employed in the catalyst, by incipient wetness, and the palladium and other metals of present are then fixed by treatment with an alkaline fixing solution by incipient wetness or roto-immersion, preferably roto immersion. The catalyst is then dried and separately impregnated with a solution of a soluble gold compound having the amount of elemental gold desired in the catalyst, and the gold is fixed by treatment with an alkaline fixing solution by incipient wetness or roto immersion, preferably incipient wetness. If the gold is to be fixed by the incipient wetness method, such fixing may be combined with the impregnation step by using a single aqueous solution of soluble gold compound and alkaline fixing compound in an amount in excess of that necessary to convert all the gold in the solution to a fixed insoluble gold compound, e.g., auric hydroxide. If a hydrocarbon such as ethylene or hydrogen is to be used in the vapor phase as reducing agent, the catalyst containing the fixed metal compounds is washed until it is free of anions, dried, and reduced with ethylene or other hydrocarbon as previously described. If hydrazine is to be used in the liquid phase as reducing agent, the catalyst containing the fixed metal compounds is treated with an aqueous solution of excess hydrazine hydrate before washing and drying to reduce the metal compounds to the free metals, and the catalyst is then washed and dried as described.

Another method of preparing the catalyst is a "modified roto-immersion" method in which only part of the gold is impregnated with the palladium and other metals, if used in a first impregnation, the metals are fixed by reaction with an alkaline fixing compound by roto-immersion, the fixed metal compounds are reduced to the free metals, e.g., with ethylene or hydrazine hydrate, with washing and drying done before an ethylene reduction or after a hydrazine reduction. The catalyst is then impregnated with the remainder of the gold in the form of a solution of water soluble gold compound, and the catalyst is again reduced, e.g., with ethylene or hydrazine, after or before washing and drying, as described previously.

After the catalyst containing palladium and gold in free metallic form deposited on a copper containing support material is prepared by any of the foregoing methods, it is advantageously further impregnated with a solution of an alkali metal acetate, preferably potassium or sodium acetate, and most preferably potassium acetate. The catalyst is then dried such that the finished catalyst contains, for example, about 10 to about 70 g/liter of catalyst, preferably about 20 to about 60 grams of alkali metal acetate per liter of finished catalyst.

When vinyl acetate is prepared using the catalysts according to the present invention, a stream of gas, which contains ethylene, oxygen or air, acetic acid, and desirably an alkali metal acetate, is passed over the catalyst. The composition of the gas stream can be varied within wide limits, taking into account explosive limits. For example, the molar ratio of ethylene to oxygen can be about 80:20 to about 98:2, the molar ratio of acetic acid to ethylene can be about 100:1 to about 1:100, and the content of gaseous alkali metal acetate can be about 2–200 ppm, relative to the acetic acid employed. The gas stream also can contain other inert gases, such as nitrogen, carbon dioxide and/or saturated hydrocarbons. Reaction temperatures which can be used are elevated temperatures, preferably those in the range of about 150–220° C. The pressure employed can be at somewhat reduced pressure, normal pressure or elevated pressure, preferably a pressure of up to about 20 atmospheres gauge.

The following non-limiting examples further illustrate the invention.

EXAMPLE 1

A support material consisting of Sud Chemie KA-160 silica spheres having a nominal diameter of about 7 mm., a surface area of about 160 to 175 $m^2$/g, and a pore volume of about 0.68 ml/g., was impregnated by the incipient wetness method with an aqueous solution of cupric nitrate trihydrate sufficient to provide the catalyst with about 1.9 grams/liter of elemental copper. Without drying, the copper was fixed on the support by treating the support by roto-immersion with an aqueous solution of sodium hydroxide containing 120% of the amount of sodium hydroxide needed to convert the copper to cupric hydroxide. The fixed cupric hydroxide-containing support was then water washed until free of anions and dried at a temperature of 100° C. or 1 hour in a fluid bed drier.

Palladium and gold were then added to the cupric hydroxide-containing support by the "separate fix" (SF) method wherein the support was first impregnated by incipient wetness with an aqueous solution of sodium palladium (II) chloride sufficient to provide about 7 grams of elemental palladium per liter of catalyst. The palladium was then fixed to the support as palladium (II) hydroxide by treating the catalyst by roto-immersion with an aqueous sodium hydroxide solution such that the Na/Cl molar ratio was about 1.2:1. The catalyst was then dried at 100° C. or 1 hour in a fluid bed drier following which it was impregnated by incipient wetness with an aqueous solution of sodium tetrachloroaurate in an amount sufficient to provide the catalyst with 4 grams/liters of elemental gold, and sodium hydroxide such that the Na/Cl mole ratio was about 1.8:1, to fix the gold on the support as auric hydroxide. The catalyst was then water washed until chloride free (about 5 hours) and dried for one hour in nitrogen flow. The copper, palladium and auric hydroxides were then reduced to the free metals by contacting the catalyst with ethylene (5% in nitrogen) in the vapor phase at 150° C. or hours. Finally the catalyst was impregnated by incipient wetness with an aqueous solution of potassium acetate in an amount sufficient to provide 40 grams of potassium acetate per liter of catalyst, and dried in a fluid bed drier at 100–150° C. or 1 hour.

EXAMPLE 2

The procedure of Example 1 was followed except that after drying, the support containing fixed cupric hydroxide and before impregnation with palladium salt solution, was calcined by heating in air at 200° C. or 18 hours.

EXAMPLE 3

The procedure of Example 2 was followed except that immediately after the cupric hydroxide containing support was calcined and before impregnation with palladium salt solution, the cupric hydroxide was reduced to metallic copper in the vapor phase by contact with ethylene (5% in nitrogen) at 150° C. or 5 hours.

EXAMPLE 4

The procedure of Example 3 was followed except that in the impregnation of the catalyst with aqueous solution of sodium tetrachloroaurate, sufficient solution was used to provide 7 rather than 4 grams of elemental gold per liter of catalyst.

EXAMPLE 5

The procedure of Example 1 was followed except that sufficient aqueous solution of cupric nitrate trihydrate was used in the initial impregnation of the support to provide 1.39 rather than 1.9 grams of elemental copper per liter of catalyst.

EXAMPLE 6

The procedure of Example 4 was followed except that after the reduction of cupric hydroxide to metallic copper, the impregnation and fixing of the catalyst with palladium and gold was accomplished by a "modified roto-immersion" (MRI) method. In this method the copper containing support was first impregnated by the incipient wetness method with a solution of palladium and gold salts sufficient to provide 7 grams of elemental palladium and 4 grams of elemental gold and the metals were fixed by roto-immersion in an aqueous sodium hydroxide solution. The catalyst was then washed until chloride free, dried at 150° C. or 5 hours in a nitrogen stream and reduced in the vapor phase with ethylene 5% in nitrogen at 150° C. or 5 hours. The catalyst was then impregnated by incipient wetness with an aqueous solution of gold salt sufficient to provide the catalyst with 3 additional grams per liter of elemental gold (for a total of 7) and sodium hydroxide such that the Na/Cl mole ratio was about 1.8:1 to fix the additional gold, and the catalyst was washed, dried, reduced with ethylene and impregnated with potassium acetate as described in Example 1.

EXAMPLE 7

The procedure of Example 6 was followed except that the support was initially impregnated with an amount of aqueous solution of copper salt to provide the catalyst with 1.39 rather than 1.9 grams/liter of elemental copper, the impregnation with the solution of palladium salt and the first increment of gold salt provided 2 rather than 4 grams/liter of elemental gold, the impregnation with the second increment of gold salt provided 2 rather than 3 additional grams/liter of elemental gold for a total of 4 rather than 7 grams/liter of gold, the reduction of palladium and the first increment of gold was done in the liquid phase using an aqueous solution of hydrazine hydrate at an excess weight ratio of hydrazine to metals of 12:1, and the reduction of the second increment of gold was done in the vapor phase with ethylene (5% in nitrogen) at 150° C. or 5 hours.

The catalysts prepared as described in Examples 1–7 were tested for their activity in the production of vinyl acetate by reaction of ethylene oxygen and acetic acid. To accomplish this about 60 ml of each type of catalyst prepared in the examples were placed in separate chrome-nickel steel baskets. The temperature of each basket was measured by a thermocouple at both the top and bottom of each basket. Each reaction basket was placed in a Berty continuously stirred tank reactor of the recirculating type and was maintained at a temperature which provided about 45% oxygen conversion with an electric heating mantle. A gas mixture of about 50 normal liters (measured at N.T.P.) of ethylene, about normal liters of oxygen, about 49 normal liters of nitrogen, about 50 gm of acetic acid, and about 40 mg of potassium acetate was caused to travel under pressure at about 12 atmospheres through each basket. The reaction was terminated after about 18 hours. Analysis of the products was accomplished by on-line gas chromatographic analysis combined with off-line liquid product analysis by condensing the product stream at about 10° C. o obtain optimum analysis of the end products.

The following table shows the results obtained with the catalyst of each example in terms of percent selectivity of $CO_2$ ($CO_2$, % sel.) and heavy ends, (HE, % sel.) and relative activity of the reaction (Act.). In addition, the table shows the palladium, gold and copper content of each catalyst in terms of grams per liter of catalyst (Pd/Au/Cu, g/L), whether the catalyst was prepared by the separate fix (SF) or modified roto-immersion (MRI) method (Meth. Cat. Prep.), and whether the palladium and gold were reduced to their metallic state with ethylene ($C_2H_4$) or hydrazine ($N_2H_4$) or both ($C_2H_4+N_2H4$) (Red Agent)

TABLE

| Example | Pd/Au/Cu, g/L | Meth. Cat. Prep. | Red. Agent | $CO_2$, % Sel. | HE, % Sel. | Act. |
|---|---|---|---|---|---|---|
| 1 | 7/4/1.9 | SF | $C_2H_4$ | 8.32 | 1.3 | 2.07 |
| 2 | 7/4/1.9 | SF | $C_2H_4$ | 8.51 | 1.16 | 1.97 |
| 3 | 7/4/1.9 | SF | $C_2H_4$ | 8.31 | 1.16 | 1.99 |
| 4 | 7/7/1.9 | SF | $C_2H_4$ | 9.37 | 1.26 | 2.16 |
| 5 | 7/4/1.39 | SF | $C_2H_4$ | 8.12 | 1.42 | 2.03 |
| 6 | 7/7/1.9 | MRI | $C_2H_4$ | 8.33 | 1.12 | 2.05 |
| 7 | 7/4/1.39 | MRI | $C_2H_4 + N_2H_4$ | 8.98 | 1.25 | 2.29 |

The results shown in the table indicate that, the catalyst of this invention generally yields a higher initial vinyl acetate productivity due to a lower $CO_2$ selectivity, than a catalyst limited to equivalent quantities of palladium and gold as catalytically active metals. However, because the copper in the catalyst of this invention is present on the surfaces of the support below the palladium and gold, the rate of loss of copper due to volatilization under the conditions of reaction is lower than is the case when the copper is intermingled with the palladium and gold, do to the simultaneous fixing or co-precipitation in the form of water-insoluble compounds such as hydroxides of intermingled water-soluble salts of copper and palladium and/or gold.

What is claimed is:

1. A process for the production of vinyl acetate by reaction of ethylene, oxygen and acetic acid comprising contacting the latter reactants with a catalyst comprising a porous support on the porous surfaces of which is deposited metallic copper in a zone surrounded by deposits of catalytically effective amounts of metallic palladium and gold, neither of which is substantially intermingled with said copper.

2. The process of claim 1 wherein said catalyst is prepared by impregnating said support with an aqueous solution of a water-soluble copper salt, fixing said copper as a water-insoluble compound by reaction with an appropriate alkaline compound, subsequently impregnating the catalyst with a one or more solutions of water-soluble salts of palladium and/or gold, the amounts of elemental palladium and gold in the total of the latter impregnating solutions being equal to the predetermined amounts of metallic palladium and gold desired in the catalyst, fixing on the catalyst the palladium and/or gold in the solution present in the catalyst after each impregnation by reacting the dissolved water-soluble salt in such solution with an appropriate alkaline compound to precipitate water-insoluble compounds of palladium and/or gold, and reducing to free metallic form the water-insoluble compounds of copper, palladium and/or gold present in the catalyst after each fixing of water-insoluble compounds of palladium and/or gold, or after the total of the latter water-insoluble compounds have been fixed on the catalyst.

3. The process of claim 1 wherein said porous support is silica.

4. The process of claim 1 wherein said catalyst contains about 0.3 to about 5.0 grams of copper per liter of catalyst.

5. The process of claim 4 wherein said amount of copper is about 0.5 to about 3.0 grams per liter of catalyst.

6. The process of claim 4 wherein said catalyst contains about 1 to 10 about grams of palladium, and about 0.5 to 10 about grams of gold per liter of catalyst, with the amount of gold being from about 10 to about 125 wt. % based on the weight of palladium.

7. The process of claim 1 wherein said catalyst also contains a deposit of an alkali metal acetate and said alkali metal acetate is also present in the feed of said reactants contacting said catalyst.

8. The process of claim 7 wherein said alkali metal acetate is potassium acetate which is present on the catalyst in an amount of about 10 to about 70 grams/liter of catalyst.

9. A process for the procuration of vinyl acetate by reaction of ethylene, oxygen, and acetic acid comprising contacting, under suitable reaction conditions, the latter reactants with a catalyst, said catalyst prepartion comprising impregnating a porous support with an aqueous solution of a water-soluble copper salt; fixing said copper as a water-insoluble compound by reaction with an appropriate alkaline compound, subsequently impregnating the catalyst with one or more solutions of water-soluble salts of palladium and/or gold the amounts of elemental palladium and gold in the total of the latter impregnating solutions being equal to the predetermined amounts of metallic palladium and gold desired in the catalyst, fixing on the catalyst the palladium and/or gold in the solution present in the catalyst after each impregnation by reacting the dissolved water-soluble salt in such with an appropriate alkaline compound to precipitate water-insoluble compounds of palladium and/or gold, and reducing to free metallic form the water-insoluble compounds of copper, palladium and/or gold present in the catalyst after each fixing of water-insoluble compounds of palladium and/or gold, or after the total of the latter water-insoluble compounds have been fixed on the catalyst.

10. A process for the production of vinyl acetate by reaction of ethylene, oxygen, and acetic acid comprising contacting, under suitable reaction conditions, the latter reactants with catalyst, prepared in accordance with claim 9, wherein further after said fixing of copper as a water-insoluble compound, the support is in sequence impregnated with a solution of a water-soluble palladium compound in the absence of any gold compound, the palladium is fixed on the support as a water-insoluble compound by reaction with an appropriate alkaline compound, the catalyst is impregnated with a solution of water-soluble gold compound, the gold is fixed on the support as a water-insoluble compound by reaction with an appropriate alkaline compound, the copper, palladium and gold in their fixed water-insoluble compounds are reduced to their free metallic form, and the catalyst is optionally impregnated with a solution of alkali metal acetate and dried.

11. A process for the production of vinyl acetate by reaction of ethylene, oxygen, and acetic acid comprising contacting, under suitable reaction conditions, the latter reactants with a catalyst prepared in accordance with claim 9 wherein further after said fixing of copper as a water-insoluble compound, the support is in sequence impregnated with a solution of an amount water-soluble palladium compound containing all of the elemental palladium desired on the finished catalyst and an amount of water-soluble gold compound part of the elemental gold desired on the finished catalyst, the palladium and gold in the latter solution is fixed on the support as water-insoluble compounds by rotating and/or tumbling the impregnated support while it is immersed in a solution of a appropriate alkaline compound, the fixed copper, palladium and gold are reduced to their free metallic state, the catalyst is impregnated with a solution of an amount of water soluble gold compound such that the total amount of elemental gold in the catalyst is equal to that desired in the finished catalyst, said latter solution also containing an amount of appropriate alkaline compound sufficient to fix the added gold as a water-insoluble compound, the fixed added gold is reduced to its free metallic state, and the catalyst is optionally impregnated with a solution of alkali metal acetate and dried.

* * * * *